United States Patent
Sadasivam et al.

(10) Patent No.: US 9,764,086 B2
(45) Date of Patent: Sep. 19, 2017

(54) METHOD AND APPARATUS FOR IDENTIFYING DISCHARGE FAILURE OF A PIEZOELECTRIC CIRCUITRY

(71) Applicant: HCL Technologies Limited, Noida, Uttar Pradesh (IN)

(72) Inventors: Siva Sakthivel Sadasivam, Tamil Nadu (IN); Shyam Thangaraju, Tamil Nadu (IN)

(73) Assignee: HCL Technologies Limited, Noida (IN)

( * ) Notice: Subject to any disclaimer, the term of this patent is extended or adjusted under 35 U.S.C. 154(b) by 0 days.

(21) Appl. No.: 15/007,065

(22) Filed: Jan. 26, 2016

(65) Prior Publication Data
US 2016/0248346 A1    Aug. 25, 2016

(30) Foreign Application Priority Data
Feb. 21, 2015   (IN) .............................. 499/DEL/2015

(51) Int. Cl.
*A61M 5/168*   (2006.01)
*H01L 41/04*   (2006.01)
*A61M 5/142*   (2006.01)

(52) U.S. Cl.
CPC .... *A61M 5/16804* (2013.01); *A61M 5/14276* (2013.01); *H01L 41/042* (2013.01); *A61M 2205/0294* (2013.01); *A61M 2205/50* (2013.01); *A61M 2205/8206* (2013.01)

(58) Field of Classification Search
CPC ............................. H01L 41/042; H02N 2/0075
See application file for complete search history.

(56) References Cited

U.S. PATENT DOCUMENTS

| | | | |
|---|---|---|---|
| 5,376,854 A * | 12/1994 | Oouchi | H01L 41/042 310/316.01 |
| 6,147,433 A | 11/2000 | Reineke et al. | |
| 6,384,512 B1 * | 5/2002 | Maeda | F02D 41/2096 310/316.03 |
| 2004/0215243 A1 * | 10/2004 | Houben | A61N 1/3787 607/5 |
| 2008/0129305 A1 * | 6/2008 | Perryman | F02D 41/2096 324/511 |
| 2009/0024042 A1 * | 1/2009 | Nunez | A61B 5/412 600/486 |

FOREIGN PATENT DOCUMENTS

| | | |
|---|---|---|
| EP | 1217667 | 6/2006 |
| JP | 2000-383108 | 6/2002 |

* cited by examiner

*Primary Examiner* — Shawki S Ismail
*Assistant Examiner* — Muhammad S Islam
(74) *Attorney, Agent, or Firm* — Knobbe Martens Olson & Bear LLP (57) ABSTRACT

The present disclosure discloses a method and apparatus for identifying discharge failure of a piezoelectric circuitry. The apparatus comprises a piezoelectric circuitry consisting of charging and discharging circuit with a microcontroller to compute the time required to charge and discharge the piezoelectric element respectively. Based on the first charging time and the second charging time corresponding to the first and second charging-discharging cycle respectively, the difference between the first and the second charging time is determined. The discharge failure in the piezoelectric circuit is identified where the first charging time is greater than the second charging time.

10 Claims, 6 Drawing Sheets

METHOD AND APPARATUS FOR IDENTIFYING DISCHARGE FAILURE OF A PIEZOELECTRIC CIRCUITRY

CROSS-REFERENCE TO RELATED APPLICATIONS

The present application claims benefit under 35 U.S.C. §119(a) to Indian Complete Patent Application No. 499/DEL/2015, filed on Feb. 21, 2015, the entirety of which is hereby incorporated by reference.

TECHNICAL FIELD

The present subject matter described herein, in general, relates to a method and apparatus for identifying discharge failure of a piezoelectric circuitry.

BACKGROUND

Piezoelectric effect is generally known as generation of electric charge in certain non-conducting material when subjected to mechanical stress such as pressure or vibration or the generation of vibration in such material when they are subjected to an electric field. This generation of electric charge resulting from pressure is commonly known as piezoelectricity. Piezoelectric elements may be solid material such as crystals, certain ceramics and biological matter such as bone, DNA and various proteins. Piezoelectric elements are capacitive consumers, which, contract or expand, depending on the charge state in each case, i.e., depending on the emerging or applied voltage.

Piezoelectricity has found use in applications of vast type and nature such as production and detection of sound, generation of high voltages, electronic frequency generation, microbalances, to drive an ultrasonic nozzle, and ultrafine focusing of optical assemblies. It is also the basis of a number of scientific instrumental techniques with atomic resolution, the scanning probe, microscopes and everyday uses such as ignition source for push-start propane barbecues, and quartz watches.

Further, piezoelectric valves use special piezoelectric mechanism that allows speedy action and also allow very precise control to the flow of fluid. Due to this nature piezoelectric valves are commonly used in medical, automobile and aeronautical industry among others. Piezoelectric valves are used in implantable medical devices such as infusion pumps that are positioned within the human body to deliver minute amount of drugs to a specified locations.

It may be understood that due to the precise nature of the piezoelectric valves/piezoelectricity and industry implementation in various medical devices it is important to identify failure in the piezoelectric valves or circuit. However, the conventional methods only identify failure conditions of piezoelectric element.

SUMMARY

Before the present apparatuses and methods, are described, it is to be understood that this application is not limited to the particular apparatus and methodologies described, as there can be multiple possible embodiments, which are not expressly illustrated, in the present disclosures. It is also to be understood that the terminology used in the description is for the purpose of describing the particular versions or embodiments only, and is not intended to limit the scope of the present application. This summary is provided to introduce aspects related to method and apparatus for identifying discharge failure of a piezoelectric circuitry and the concepts are further described below in the detailed description. This summary is not intended to identify essential features of subject matter nor is it intended for use in determining or limiting the scope of the subject matter.

In one implementation, apparatus for identifying failure of a circuit adapted to discharge a piezoelectric element is disclosed. In one aspect, the apparatus may comprise a piezoelectric circuitry comprising a charging circuit and a discharging circuit adapted to charge and discharge a piezoelectric element respectively. Further, the apparatus may comprise a microcontroller. In one aspect, the microcontroller is configured to determine a first charging time and a first discharging time corresponding to a first cycle associated with the charging and the discharging of the piezoelectric element. The microcontroller is further configured to determine the second charging time and a second discharging time corresponding to a second cycle associated with the charging and the discharging of the piezoelectric element. The apparatus compares the second charging time with the first charging time. The apparatus may further identify failure in the discharging circuit wherein the failure in the discharging circuit occurs if the difference between the first charging time and the second charging time is greater than a predefined threshold value.

In another implementation, a method for identifying failure of a circuit adapted to discharge a piezoelectric element is disclosed. In one aspect, the method may comprise determining, by a microcontroller, a first charging time corresponding to a first cycle associated with the charging and the discharging of the piezoelectric element. Further, determining, by a microcontroller, a second charging time and a second discharging time corresponding to a second cycle associated with the charging and the discharging of the piezoelectric element. The microcontroller compares the second charging time with the first charging time. The method may further identify, by a microcontroller, failure in the discharging circuit wherein the failure in the discharging circuit occurs if the difference between the first charging time and the second charging time is greater than a predefined threshold value.

BRIEF DESCRIPTION OF THE DRAWINGS

The foregoing detailed description of embodiments is better understood when read in conjunction with the appended drawings. For the purpose of illustrating the disclosure, there is shown in the present document example constructions of the disclosure. However, the disclosure is not limited to the specific methods and apparatus disclosed in the document and the drawings.

The detailed description is described with reference to the accompanying figures. In the figures, the left-most digit(s) of a reference number identifies the figure in which the reference number first appears. The same numbers are used throughout the drawings to refer like features and components.

DETAILED DESCRIPTION

The exemplary embodiments of the present disclosure are described herein in detail, though the present disclosure is not limited to these embodiments. Various modifications to the embodiment will be readily apparent to those skilled in the art and the generic principles herein may be applied to other embodiments. However, one of ordinary skill in the art will readily recognize that the present disclosure is not intended to be limited to the embodiments illustrated, but is to be accorded the widest scope consistent with the principles and features described herein.

The words "comprising", "having", "containing", and "including", and other forms thereof, are intended to be equivalent in meaning and be open ended in that an item or items following any one of these words is not meant to be an exhaustive listing of such item or items, or meant to be limited to only the listed item or items. It must also be noted that as used herein, the singular forms "a", "an", and "the" include plural references unless the context clearly dictates otherwise. Although any apparatus and method similar or equivalent to those described herein can be used in the practice or testing of embodiments of the present disclosure, the exemplary, apparatus and methods are now described.

While aspects of described method and apparatus for identifying discharge failure of a piezoelectric circuitry in a medical implantable device may be implemented in any number of different apparatus and/or configurations, the embodiments are described in the context of the following exemplary apparatus.

Figure 1:
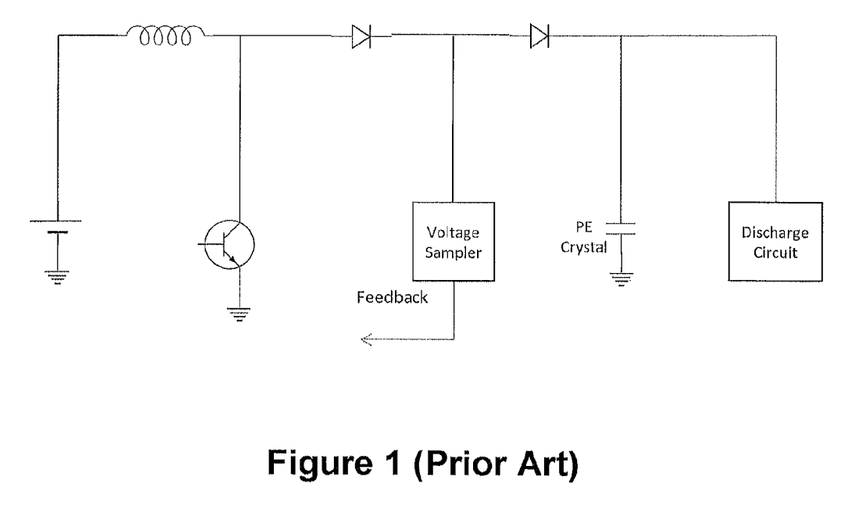
FIG. 1 illustrates a conventional current system in piezoelectric circuitry in accordance with prior art.

Referring to FIG. 1, the figure illustrates a conventional current system in piezoelectric circuitry as known to a person skilled in the art.

Figure 2:
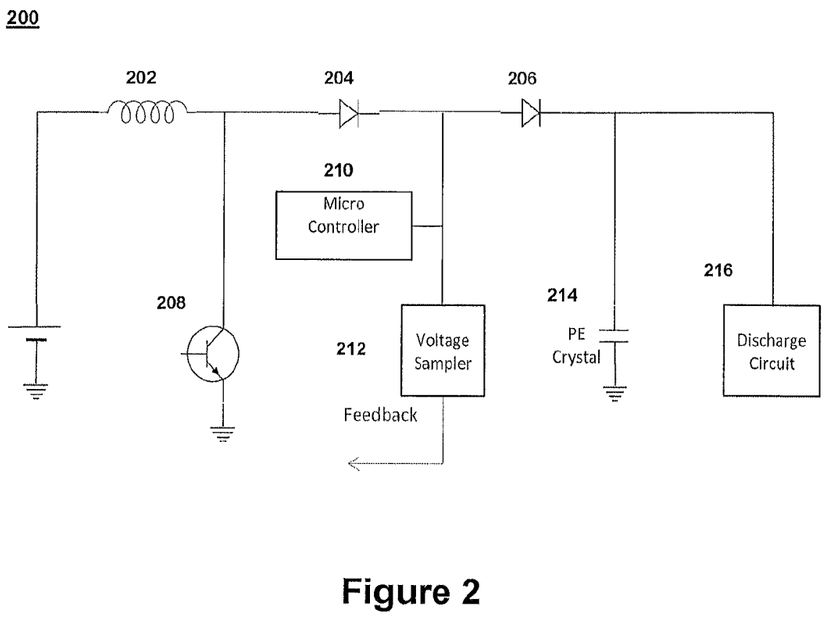
FIG. 2 illustrates the current system in piezoelectric circuitry, in accordance with an embodiment of the present disclosure.

Now referring to FIG. 2, a piezoelectric circuitry 200 integrated with various components is shown in accordance with one embodiment of the present disclosure. As illustrated, an apparatus for identifying discharge failure of a piezoelectric circuitry is disclosed. The apparatus may comprise components like piezoelectric element 214 connected in a piezoelectric circuit 200 wherein the piezoelectric element acts as a capacitor to store electric charge under high voltage. The apparatus may further comprise a charging circuit and a discharging circuit 216. The charging circuit may include a charging switch/transistor 208, a charging coil/inductor 202, multiple diodes 204 and 206, piezoelectric element 214 connected in series. A voltage sampler 212 along with the self-diagnosis module is introduced in the charging circuit between the charging coil/inductor 202 and the piezoelectric element 214 to determine the voltage through the circuit and further transmit the feedback to the transistor controlling the inductor. The voltage sample 212 may further comprise a microcontroller 210 to compute the time required to charge and discharge the piezoelectric circuit 200. The charging switch/transistor 208 may further comprise a pulse-width modulation (PWM) control unit within the circuit. The discharging circuit may include a discharging switch, a diode, a discharging coil and piezoelectric element, connected in series. Further, the piezoelectric circuitry is divided in multiple sectors by diodes to prevent reversal and unwanted flow of current. The diode of the charging circuit prevents the flow of a current in the charging circuit, which would discharge the piezoelectric element.

In accordance with an embodiment, the current flows though the diode 204, 206 and charges the piezoelectric element 214 in another sector when the transistor 208 is in 'ON' state. In the 'ON' state the inductor 202 in the circuitry is charged by the battery which further charges the piezoelectric element 214 on switching of the transistor 208. The battery in general is the voltage source for the piezoelectric element. In one aspect, the transistor 208 uses a pulse-width modulation (PWM) waveform to control the charging of the piezoelectric element. The PWM provides the pulse signal to determine the time required for the piezoelectric element to reach a predetermined voltage.

Figure 3:
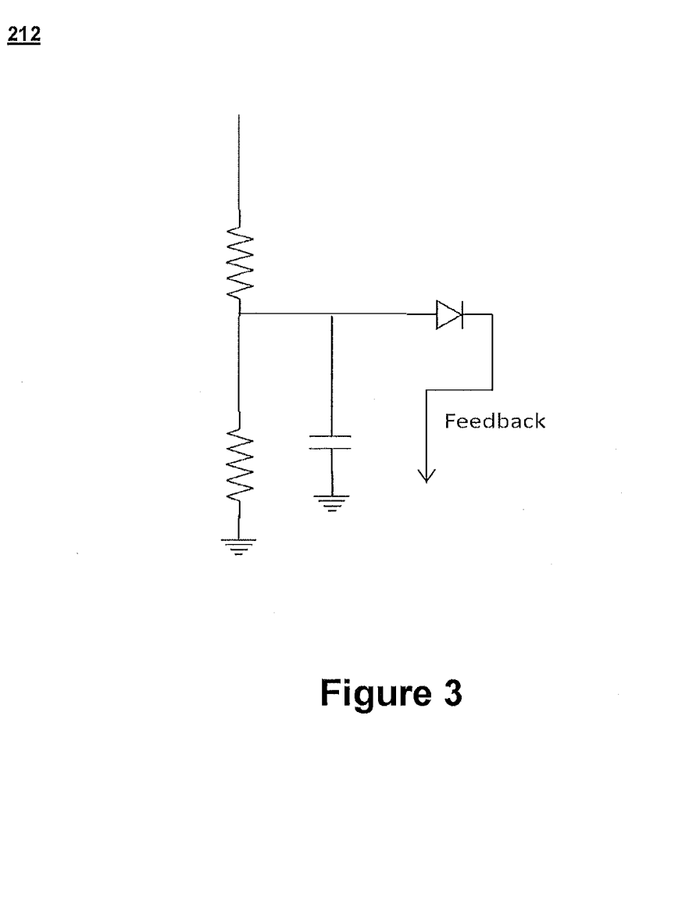
FIG. 3 illustrates the voltage sampler and feedback circuitry, in accordance with an embodiment of the present disclosure.

Still referring to FIG. 2, voltage sampler 212 comprises a self-diagnosis module that may be positioned with the timing system of microcontroller 210 to measure the time required by the piezoelectric circuitry 200 to build its charge from zero to a predetermined voltage along with the other parameters. Further, the microcontroller 210 driven in voltage sampler 212 allows measuring the duration of charge cycle. FIG. 3 illustrates the voltage sampler 212 and feedback circuitry, in accordance with an embodiment of the present disclosure.

Figure 4:
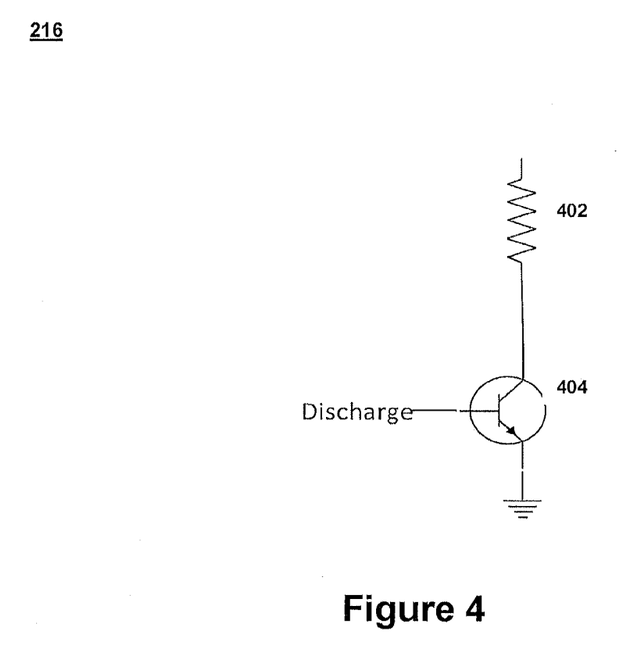
FIG. 4 illustrates the discharge circuitry, in accordance with an embodiment of the present disclosure

In accordance with an embodiment, after the piezoelectric element 214 has reached a predetermined voltage the voltage sampler 212 signals the transistor 208 which then goes to the 'OFF' state. In the 'OFF' state the piezoelectric element 214 discharges the voltage gained in the charging phase to return to the charge state of zero. Further, the discharge circuit 216 is activated. Referring to FIG. 4, a discharge circuitry 216 integrated with various components is shown in accordance with one embodiment of the present disclosure. As illustrated, a discharge circuitry 216 may comprise components like discharge switch 404 and resistance 402.

Figure 5:
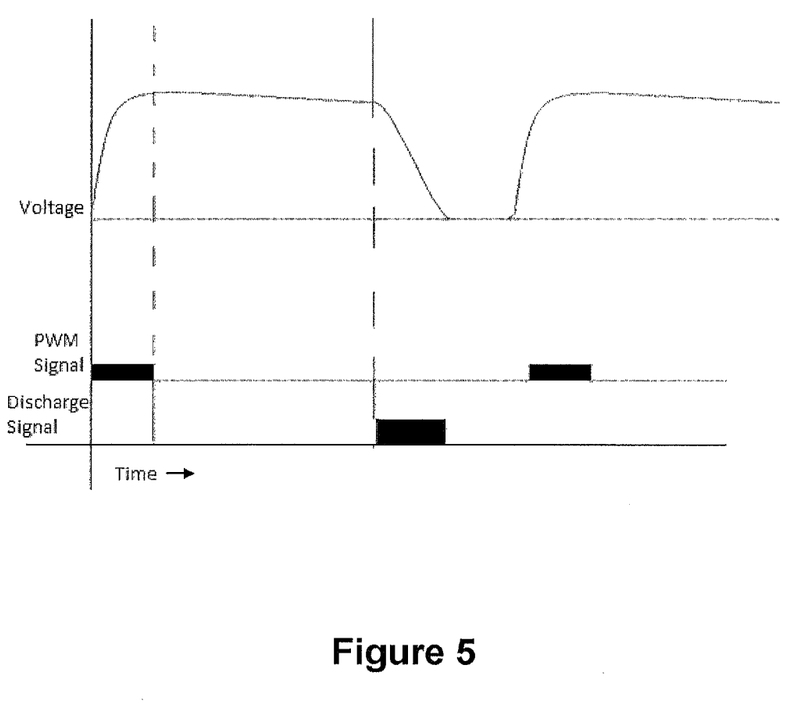
FIG. 5 illustrates a normal voltage gain curve, in accordance with an embodiment of the present disclosure.

In particular, the charging circuit and discharging circuit 216 are repeatedly opened and closed during the charging and discharging phase respectively. In this continuous charging and discharging cycle the time required by the piezoelectric element to subsequently charge to a predetermined voltage is measured by the microcontroller. FIG. 5 illustrates a normal voltage gain curve, in accordance with an embodiment of the present disclosure. Referring to the FIG. 5, the figure illustrates the PWM waveform for the time required to reach the predetermined voltage during the charging phase and the time required to discharge from the predetermined voltage and so on for a piezoelectric element.

For the purpose of the present disclosure, the microcontroller 210 may be configured to determine the first charging time and first discharging time corresponding to a first cycle associated with the charging and the discharging of the piezoelectric element 214. Further, the microcontroller 210 may determine the second charging time and second discharging time corresponding to a second cycle associated with the charging and the discharging of the piezoelectric element. The microcontroller 210 is configured to store the charge and discharge time values in the appropriate locations, and regulates, according to the data. The use of microprocessor 210 for performing timing functions is of particular significance for execution of the invention. The present invention is of particular importance to identify abnormality in the discharge circuit leading to discharge failure of a piezoelectric circuitry based on the comparison between the time required to charge the piezoelectric element in the first cycle and time required to charge the piezoelectric element in the second charging cycle measured by a microcontroller 210.

It is to be understood that in the circumstance of a discharge circuitry 216 failure the piezoelectric element shall not be fully discharged and would still hold the voltage gained during the charging cycle. It will further be appreciated that a piezoelectric element 214 holds voltage and hence, cannot be connected to a voltage sampler 212 within its sector, as the repeated sampling itself shall drain the piezoelectric element.

In accordance with an embodiment, due to the failure in the discharge circuit 216 the piezoelectric element 214 is not fully discharged and thus will not follow a normal curve of charge and discharge phase as illustrated in the FIG. 5 in accordance with an embodiment of the present disclosure.

In the piezoelectric circuitry the circumstance of discharge failure in discharge circuit occurs if the difference between the first charging time and the second charging time is greater than a predefined threshold value. Due to the piezoelectric element still holding the charge the time required to charge the piezoelectric element during the second cycle shall be less than the time required to charge during the first cycle. The failure may be determined by the microcontroller 210 based on the time difference in the first charging time and the second charging time. The time difference is calculated by the timing system of the microcontroller 210 introduced in the voltage sampler to measure the time required by the piezoelectric circuitry to build its charge from zero to predetermined voltage. The failure in discharge circuit 216 may be further indicated by the microcontroller 210 to the user by employing various known alert mechanisms.

Figure 6:
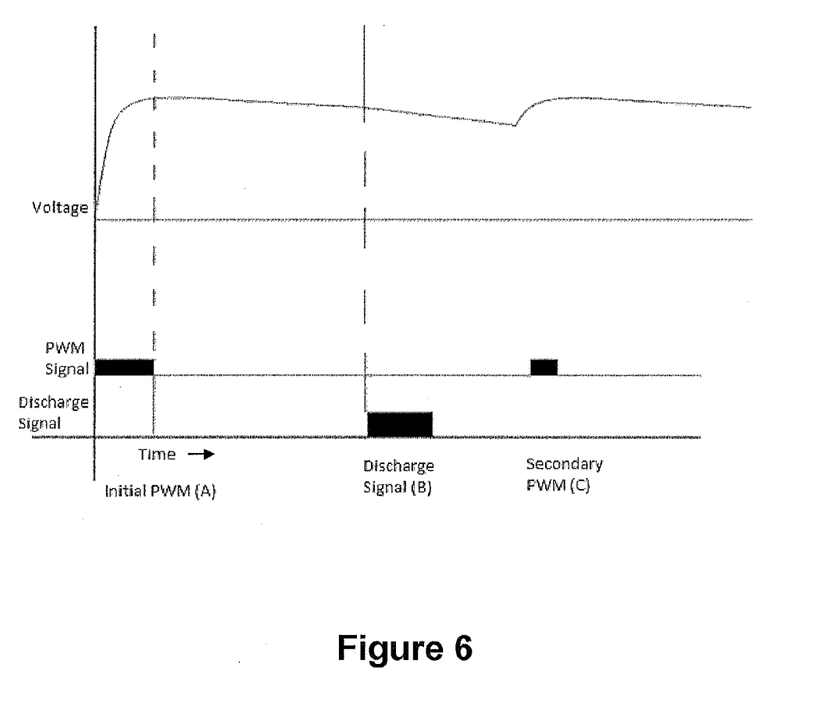
FIG. 6 illustrates the discharge failure curve, in accordance with an embodiment of the present disclosure.

In order to understand the working of the timing system of the microcontroller 210, consider an example wherein the time required to charge the piezoelectric element is 'T' in the first charge cycle and the time required to charge the piezoelectric element is 'T-X' in the second charge cycle. Wherein T is greater than T-X respectively in condition of discharge circuitry failure. Due to the difference in the time required to charge the piezoelectric element 214 is less in the second charge cycle as compared to the charge time required to charge the piezoelectric element in first charge cycle it is determined that the failure has occurred in the discharge circuitry 216 of the piezoelectric circuit 200. FIG. 6 illustrates the discharge failure curve, in accordance with an embodiment of the present disclosure. The Table 1 below provides experimental data of a failure condition in the discharge circuitry.

| S. No | Initial PWM (A) | Discharge Signal (B) | Secondary PWM (C) |
|---|---|---|---|
| 1 (New piezoelectric element) | 250 ms | 150 ms | 15 ms |
| 2 | 260 ms | 160 ms | 15 ms |
| 3 | 340 ms | 160 ms | 20 ms |
| 4 | 380 ms | 160 ms | 20 ms |
| 5 | 400 ms | 160 ms | 20 ms |
| 6 | 500 ms | 170 ms | 25 ms |
| 7 | 550 ms | 170 ms | 25 ms |
| 8 (Aged piezoelectric element) | 600 ms | 170 ms | 25 ms |

Although implementations for methods and apparatus for identifying discharge failure of a piezoelectric circuitry have been described in language specific to structural features and/or methods, it is to be understood that the appended claims are not necessarily limited to the specific features or methods described. Rather, the specific features and methods are disclosed as examples of implementations for identifying discharge failure of a piezoelectric circuitry.

Thus, in this manner explained, the aforementioned apparatus and methodology are advantageous for identifying discharge failure of a piezoelectric circuitry using minimum input details and complicated computational analysis. The method and apparatus can be used in multiple areas but particularly in implantable medical device such as infusion pumps that are required to deliver minute amount of drugs to specified location and the like.

We claim:

1. An apparatus for identifying failure of a circuit adapted to discharge a piezoelectric element, the apparatus comprising:
   a piezoelectric circuitry comprising a charging circuit and a discharging circuit adapted to charge and discharge a piezoelectric element respectively, wherein the piezoelectric circuitry further comprises a microcontroller configured to:
   determine a first charging time and a first discharging time corresponding to a first cycle associated with the charging and the discharging of the piezoelectric element;
   determine a second charging time and a second discharging time corresponding to a second cycle associated with the charging and the discharging of the piezoelectric element;
   compare the second charging time with the first charging time; and
   identify failure in the discharging circuit wherein the failure in the discharging circuit occurs if the difference between the first charging time and the second charging time is greater than a predefined threshold value.

2. The apparatus of claim 1, wherein the charging circuit is connected with a transistor wherein the transistor uses a pulse-width modulation waveform to control the charging of the piezoelectric element.

3. The apparatus of claim 1, wherein the microcontroller is connected in voltage sampler to compute the time required to charge and discharge the piezoelectric circuit.

4. The apparatus of claim 3, wherein the voltage sampler is further connected to a timing system to measure the time required by the piezoelectric circuitry to build its charge from zero.

5. The apparatus of claim 1, wherein the apparatus is embedded in an implantable medical device.

6. A method for identifying failure of a circuit adapted to discharge a piezoelectric element, the method comprising:
   determining, by a microcontroller, a first charging time and a first discharging time corresponding to a first cycle associated with the charging and the discharging of the piezoelectric element;
   determining, by the microcontroller, a second charging time and a second discharging time corresponding to a second cycle associated with the charging and the discharging of the piezoelectric element;
   comparing, by the microcontroller, the second charging time with the first charging time; and
   identifying, by the microcontroller, failure in the discharging circuit wherein the failure in the discharging circuit occurs if the difference between the first charging time and the second charging time is greater than a predefined threshold value.

7. The method of claim 6, wherein the charging circuit is connected with a transistor wherein the transistor uses a pulse-width modulation waveform to control the charging of the piezoelectric element.

8. The method of claim 6, wherein the microcontroller is connected in voltage sampler to compute the time required to charge and discharge the piezoelectric circuit.

9. The method of claim 8, wherein the voltage sampler is further connected to a timing system to measure the time required by the piezoelectric circuitry to build its charge from zero.

10. The method of claim 6, wherein the apparatus is embedded in an implantable medical device.

\* \* \* \* \*